United States Patent [19]

Tanimoto

[11] Patent Number: 5,403,736
[45] Date of Patent: Apr. 4, 1995

[54] METHOD OF INDUCING FORMATION OF ADVENTITIOUS BUD

[75] Inventor: Shizufumi Tanimoto, Hiroshima, Japan

[73] Assignee: Mitsui Petrochemical Industries, Ltd., Tokyo, Japan

[21] Appl. No.: 53,765

[22] Filed: Apr. 28, 1993

Related U.S. Application Data

[63] Continuation-in-part of Ser. No. 492,390, Mar. 8, 1990, abandoned, which is a continuation of Ser. No. 162,520, Mar. 1, 1988, abandoned.

[30] Foreign Application Priority Data

Mar. 6, 1987 [JP] Japan .................................. 62-50215
Jul. 3, 1987 [JP] Japan ................................. 62-165196

[51] Int. Cl.$^6$ ............................................. C12N 5/04
[52] U.S. Cl. ............................. 435/240.45; 435/240.4; 435/240.54
[58] Field of Search ............ 435/240.4, 240.45, 240.54; 47/58.18, 58.24

[56] References Cited

PUBLICATIONS

Tanimoto, et al (1986) Plant Cell Physiol. 27(1):1–10.
Murashige, et al (1982) Physiologia Plantarum 15: pp. 473, 476 & 485.
Chih-Ching, et al. (Sep.–Oct. 1975) Scientia Sinica 18(5) pp. 659, 667.
Gamborg, et al. (1968) Experimental Cell Research 50:151,152.

*Primary Examiner*—Che S. Chereskin
*Attorney, Agent, or Firm*—Nixon & Vanderhye

[57] ABSTRACT

Formation of adventitious buds, adventitious embryos and plant bulblets are induced by mechanically making fine openings in plant tissue pieces or callus and introducing calmodulin and/or calcium ions into the plant tissue pieces or callus then culturing in an artificial culture medium.

6 Claims, No Drawings

METHOD OF INDUCING FORMATION OF ADVENTITIOUS BUD

CROSS-REFERENCE TO RELATED APPLICATIONS

This application is a continuation-in-part of our earlier application Ser. No. 07/492,390, filed Mar. 8, 1990, now abandoned, which in, turn is a continuation of application Ser. No. 07/162,520, filed Mar. 1, 1998, now abandoned.

BACKGROUND OF THE INVENTION

1. Field of the Invention

The present invention concerns a method of inducing the formation of adventitious buds, adventitious embryos or bulblets of a plant by applying tissue culture to plants in a specific method.

2. Description of the Prior Art

Vegetables, such as cabbages, tomatoes and cucumbers as well as rices have been utilized for foods, while on the other hand, horticultural plants such as tulips, bluebottle and rudbeckia have been favored as ornamental plants. These plants have been multiplied traditionally by seedlings, division of bulbs or tubers, etc. However, such multiplying methods not only require a large area and much labor, they also involve problems of reduction of seedling growing rate or degradation in the quality of flowers due to the spread of virus diseases in recent years. To maintain and promote superior properties of plants, a vegetative propagation may be suitable. With the aim of avoiding these problems, improving the overall process and increasing multiplication efficiency, methods utilizing the techniques of plant tissue culture have also been reported in recent years (for example, refer to Japanese Patent Laid-Open No. Sho 55-14734). Multiplication by tissue culture techniques has been attained by way of differentiation of adventitious buds, adventitious embryos, bulbs, etc. from cultured tissue pieces and cultured cells and it has been considered that the differentiation is controlled by the concentration ratio between cytokinin and auxin as a plant hormone (for example, refer to Annals of Botany vol. 45, 321–327, 1980). However, there are many kinds of plant groups which cause no differentiation by plant hormones only and the frequency of differentiation therein, if it occurs, is extremely low. A more direct and effective method of inducing the differentiation is still needed.

The present inventors have investigated more efficiently multiplying seedlings of plants as compared with the usual case based on the recognition that there are various problems in plant tissue culture techniques as described above.

As a result, the present inventors have found those substances for promoting the differentiation of adventitious buds, adventitious embryos and bulbs of the plants acting on the plant cells and then found a method of multiplying the seedlings of plants efficiently based on these findings. That is, the method according to the present invention provides a method of inducing formation of adventitious buds, adventitious embryos or bulblets of a plant and a way of multiplying seedlings of plants by applying tissue culture after introducing calmodulin and/or calcium into the cells of plant tissue pieces or callus of the plants.

The plants that can be treated with the method of tissue culture according to the present invention are not restricted so the method can be applied to all kinds of plants.

Those plants to which the method according to the present invention can be applied include, for example, Papaveraceae, Solanaceae, Umbelliferae, Rosaceae, Liliaceae, Compositae, Geraniaceae, Cucurbitaceae and Gramineae. Specific examples of such plants include those described in "Ground for the plants System Classification" edited by Yamagishi, published by Kokuryukan in 1974. More specifically, there can be mentioned those plants belonging to the family Solanaceae such as eggplant, tomato, potato, sweet potato and basil; plants belonging to Papaveraceae such as poppy, rape, cabbage, radish, Chinese cabbage; plants belonging to Umbelliferae such as carrot, Japanese parsley and parsley, plants belonging to Rosaceae such as rose, strawberry, soybean and cherry; plants belonging to Liliaceae except for Lilium such as onions and tulips, plants belonging to Compositae such as chrysanthemum, bluebottle and sunflower; plants belonging to Geraniaceae such as pelargonium, geranium and flax, plants belonging to Cucurbitaceae such as cucumber and pumpkin; and plants belonging to Gramineae such as rice and corn. Among these plants relevant to the present invention, preferred plants are, specifically, tomato, tobacco, eggplant, trenia, carrot, cabbage, onion, soybean, basil, bluebottle, rudbeckia, carnation, trumpet lily, tulip, asparagus, flax, cucumber and rice.

In the present invention, the tissue culture of plants can be conducted by using tissue pieces or callus of the plant. The tissue culture pieces can include, specifically, tissue pieces of plants prepared by slicing cotyledon, hypocotyl, shoot apex, stalk, leaf, scale or root of other tissue. These tissue pieces are used usually after sterilization with sodium hypochlorite or ethanol. However, in the case of using an aseptically cultured plant, the above-mentioned sterilized procedure is not required. Further, in the case of multiplying seedlings of plants with no diseases and viruses, tissues near the apical point and tissue pieces of the plants obtained from the tissue near the apical point can be used as the culture material. The cultured cells that can be used in the tissue culture of the plants in the present invention are obtained from any available portion of the plant and are non-differentiated amorphous cells including callus tissue obtained by applying tissue culture to the tissue pieces by the known method.

In the present invention, for forming a seedling of a plant by the tissue culture of tissue pieces or cultured cells of the plant thereby forming the seedling, the method as specifically described below is used.

In the method of applying tissue culture according to the present invention, tissue culture is applied after introducing calmodulin and/or calcium into the cells of the tissue pieces or callus.

Calmodulin used in the present invention is a sort of protein such as $Ca^{2+}$-ATPase of an erythrocyte membrane or phosphodiesterase of the brain having an activating function, the mobility of which is reduced in the presence of calcium upon conducting electrophoresis. Calmodulin can be isolated and purified for example, from bulbs of trumpet Lily, cerebrum of cattle, seminal vesicle of rat, etc.

As a specific illustration of the present invention of applying tissue culture after introducing calmodulin and/or calcium into the cells is now described. (1) The tissue culture method according to the present invention provides a method of applying tissue culture after introducing a specific protein referred to as calmodulin into the cells of tissue pieces or callus of plants.

The method of introducing calmodulin according to the present invention can include, for example, the following methods. The calmodulin introducing treatment is carried out by placing tissue pieces or callus of a plant to be subjected to tissue culture between electrodes and, after adding a solution containing calmodulin thereto, electrical pulses at from 30 V/cm to 2.5 KV/cm of electrical field intensity are applied for 30 $\mu$sec to 1 msec. In this case, calmodulin present in the solution is desirably used at a concentration usually from 3 $\mu$g/ml to 1 mg/ml. In addition to the electrical injection process as described above, there can be mentioned various ways techniques for injecting a solution containing calmodulin into the inside of the cells by using a micropipet made of glass under microscopic observation, a method of irradiating laser beam pulses to the cells placed in a calmodulin-containing solution to punctuate fine pores of submicron diameter to the cells and introducing calmodulin through the holes to the inside of the cells by using a method of transporting the material to the inside of the living cells as described Japanese Patent Publication No. Sho 62-7838, or a method of introducing macromolecules to the inside of plant cells by using tungsten bullets reported recently, etc. The amount of calmodulin introduced to the inside of the cells by the methods described above in the present invention can be determined by labelling the calmodulin with a fluorescent dye and measuring the fluorescence intensity after introduction to the inside of the cells. The amount is within a range usually from 1 $\mu$g/ml to 300 $\mu$g/ml and, preferably, from 10 $\mu$g/ml to 100 $\mu$g/ml.

In the method of applying tissue culture after mechanically introducing calmodulin to the inside of the cells of tissue pieces or callus of plants according to the present invention, tissue culture may be applied using a culture medium prepared by adding calcium ions at a concentration usually greater than 1 mM to the medium described later, after the introduction of calmodulin. In addition, after the introduction of calmodulin, tissues or calluses may be cultured using a culture method such as proposed in U.S. patent application Ser. No. 07/162,520(Japanese Patent Laid-Open Application No. Sho 63-279,772) according to the present inventors. That is, tissue culture may be applied using a culture medium containing calcium ionophores such as A23187 within the range from $10^{-8}$ to $10^{-4}$M, preferably from $10^{-7}$ to $10^{-5}$M. In addition, after tissue culture was applied by using a culture medium containing calcium ionophores such as A23187 within the range from $10^{-8}$ to $10^{-4}$M, the tissue pieces or callus of plants may be further cultured by mechanically adding calmodulin. (2) The tissue culture according to the present invention provides a method of applying tissue culture after introducing calcium ion into the cells of tissue pieces or the callus of plants.

The calcium introduction method according to the present invention can be conducted in the same manner as in the case of introducing calmodulin. For instance, in the case of electrical injection, the tissue pieces or callus of a plant are put between electrodes, an aqueous solution containing calcium ion is added and, thereafter, pulses are applied to introduce calcium ion to the inside of the cells of the tissue pieces or callus.

The calcium ion concentration in the solution in this case, is usually within a range from 100 $\mu$M to 30 mM.

The solution containing calcium ion can include, specifically, those aqueous solutions containing dissolved therein calcium compounds such as calcium chloride, calcium nitrate and calcium carbonate. In the present invention, the amount of calcium ion introduced to the inside of the cells by the above-mentioned method, when expressed in the same manner as for calmodulin, is within a range usually from $10^{-8}$M to $10^{-5}$M and, preferably, from $10^{-6}$M to $10^{-5}$M. (3) The tissue culture method of the present invention provides a method of applying tissue culture after introducing calmodulin and calcium into the cells of tissue pieces or cultured cells of plants.

The above-mentioned method is particularly preferred in the present invention since the differentiation for the adventitious buds and adventitious embryos of plants is remarkably promoted as compared with the methods (1), (2) above. The calmodulin and calcium ion can be introduced into the cells by the same procedures as in the case of (1) and (2) mentioned above and introduction can be attained, for instance, by placing the tissue pieces or callus of plants between electrodes and, after adding a solution containing calcium ion and calmodulin, applying pulses at the same electrical field intensity as above in the same manner. In this case, the concentrations for the calmodulin and calcium ion in the solution are within the same ranges as those in (1) and (2) above. Further, the amounts of calmodulin and calcium ion introduced to the inside of the cells are also within the range of (1) and (2) described above.

Upon introducing calmodulin and calcium ion to the inside of cells of the tissue pieces or callus in the present invention, it is usually desirable to simultaneously introduce calcium ion and calmodulin at the same time using a solution containing calcium ion and calmodulin as described above. It is also possible to separately introduce calmodulin and calcium, as required, to the inside of the cells by the method as described above, etc., followed by applying tissue culture.

Culture medium used for the tissue culture applied after the introduction of calmodulin and/or calcium can include, for example, those culture media as specifically described later.

The culture medium used in the present invention contains inorganic ingredients and a carbon source as the essential ingredients, to which plant hormones and vitamins and, as required, amino acids are added. The inorganic ingredients for the culture medium can include those inorganic salts including elements such as nitrogen, phosphorus, potassium, sodium, calcium, magnesium, sulfur, iron, manganese, zinc, boron, molybdenum, chlorine, iodine and cobalt. Specifically, these compounds include potassium nitrate, sodium nitrate, ammonium nitrate, ammonium chloride, potassium chloride, calcium chloride, potassium monohydrogen phosphate, sodium dihydrogen phosphate, magnesium sulfate, magnesium chloride, sodium sulfate, ferrous sulfate, ferric sulfate, manganese sulfate, copper sulfate, sodium molybdate, molybdenum trioxide, potassium iodide, zinc sulfate, boric acid and cobalt chloride.

The carbon source for the culture medium can include, for example, carbon hydrate and derivatives thereof such as sucrose, organic acids such as fatty acid and primary alcohols such as ethanol.

Plant hormones for the culture medium can include, for example, auxins such as naphthalene acetic acid (NAA), indole acetic acid (IAA), p-chlorophenoxyacetic acid, 2,4-dichlorophenoxy acetic acid (2,4-D), indole butyric acid (IBA) and derivatives thereof, and cytokinins such as benzyl adenine (BA), kinetin, zeatin, etc.

Vitamins for the culture medium can include, for example, biotine, thiamine (vitamin B1), pyridoxine (vitamin B6), pyridoxal, pyridoxamine, calcium pantotate, ascorbic acid (vitamin C), inositol, nicotinic acid, nicotinic amide and riboflavine (vitamin B2).

The amino acid for the culture medium can include, for example, glycine, alanine, glutamic acid, cystein, phenyl alanine and lysine.

The culture medium of the present invention desirably contains from about 0.1 $\mu$M to about 100 mM of the inorganic ingredient, from about 1 g/l to about 100 g/l of a carbon source, from about 0.01 mg/l to about 10 mg/l of plant hormones, from about 0.1 mg/l to about 150 mg/l of vitamins and from 0 to about 1000 mg/l of amino acids.

The culture medium used for the tissue culture according to the present invention can include specifically those known culture media used for the tissue culture, for example, Murashige & Skoog culture medium ('62), Linsmaier & Skoog culture medium (RM-1965), White culture medium ('63), Gamborg B-5 culture medium, Mitsui M-9 culture medium, Nitch & Nitch culture medium, etc., such media being incorporated as required with the carbon source and plant hormone as described above and, further, vitamins and amino acids as described above. Among them, those culture media prepared by using Nitch & Nitch, Linsmaier & Skoog or Marushige-Skoog media are preferred. In the present invention, it is also possible to use a culture medium prepared by adding calcium ionophore, cyclic AMP and polyamine as proposed in Japanese Patent Laid-open Application No. Sho 631-2779722 mentioned above. The compositions of the known culture media mentioned above are described, for example, in "New Plant Tissue Culture" P386–P391, written by Takeuchi, Nakajima, Furuya, and published by Asakura Shoten in 1979.

The culture medium usable in the present invention is a liquid culture medium or solid culture medium usually containing from 0.1 to 2% of a gelling agent such as agar or Gelite.

In the present invention, the tissue pieces or callus of plants as described above can be subjected to tissue culture by using a liquid culture medium aerated with oxygen-containing gas in the same manner as described in Japanese Patent Laid-Open Application No. Sho 61-285928 of the present applicant.

According to the method of the present invention, it is possible to obtain a great number of adventitious buds, adventitious embryos, bulblets (small bulbs), etc. at high efficiency from tissue pieces or callus of plants. Adventitious buds obtained by the method according to the present invention can be rooted into plant bodies, which are then sliced into tissue pieces (bulblets are also sliced) and subjected further to the tissue culture by the culture method as described above according to the present invention thereby enabling one to multiply seedlings in a significant amount.

Further, the plants obtained by the present invention can be grown into intact, stable plant bodies by the usual cultivation.

Using the present invention, in which tissue culture is applied after introducing calmodulin and/or calcium into the cells of tissue pieces of or callus of plants, since the differentiation of adventitious buds, adventitious embryos and bulbs of plants is remarkably promoted, a great number of seedlings can be multiplied. Accordingly, by the method of the present invention, plant bodies of high quality can be cultured in a great number at higher efficiency as compared with the conventional method from the tissue pieces or callus of plants thereby enabling one to multiply seedlings in great number. Furthermore, by the use of the method according to the present invention, the grown stalks from the differentiated adventitious buds can have lager diameter stalks and one can obtain a good seedlings for that reason.

EXAMPLE

The invention is further explained with reference to the following non-limiting examples.

Example 1

After sterilizing the scales of trumpet lily bulbs with 70% ethanol and an aqueous solution of sodium hyporchlorite (effective chlorine amount 1%) and cutting into about 2 mm width, pieces were placed between electrodes, to which were added 3 mM aqueous solution of calcium chloride containing 100 $\mu$g/ml of calmodulin isolated and purified from the bulbs of trumpet lily. The pieces were pulsed three times at 500 V/cm of electric field intensity for 200 $\mu$sec. Then, aseptic Murashige and Skoog solid culture medium (1962) (Gelite concentration, 0.2%) at pH 6.0 containing 4% sucrose, 0.01 mg/liter of naphthalene acetic acid and 0.02 mg/liter of benzyl adenine was prepared. 10 pieces of the trumpet lily bulb scales described above were added to the medium and cultured at 25° C. in a bright place for 3 weeks. The results, as shown in Table 1, were reported as the number of bulbs formed per slice. The number of bulbs obtained by differentiation was increased in all of the treated specimens as compared with those in Comparative Example 1.

Comparative Example 1

Slices of trumpet lily scales were cultured using the same procedures as in Example 1 except for using distilled water instead of the calcium chloride solution containing calmodulin in Example 1.

Examples 2–3

Tissue culture was applied to trumpet lily using the same procedures as in Example 1 except for using slices of trumpet lily leaves or callus cells of the trumpet lily instead of slices of trumpet lily scales as the material in Example 1, to obtain the results as shown in Table 1. The number of differentiated bulbs was increased in all of the treated specimens as compared with those in Comparative Examples 2–3.

Comparative Examples 2–3

Slices of trumpet lily leaves and callus cells of trumpet lily were cultured using the same procedures as in Examples 2–3 except for using distilled water instead of the calcium chloride solution containing calmodulin in Example 2–3 and results are shown in Table 1.

Examples 4–5

Tissue culture was applied to callus cells of trumpet lily using the same procedures as in Example 3 except for using calmodulin isolated and purified from cattle cerebrum or rat seminal vesicles as the calmodulin. The results are shown in Table 1.

TABLE 1

|  | Material | Treatment | Number of bulbs formed / slice |
|---|---|---|---|
| Example 1 | Slice of trumpet lily scales | Treated with introduction of calmodulin and $Ca^{2+}$ | 4.7 |
| Comparative Example 1 | Slice of trumpet lily scales | Treated with introduction of distilled water | 2.1 |
| Example 2 | Slice of trumpet lily leaves | Treated with introduction of calmodulin and $Ca^{2+}$ | 12.8 |
| Example 3 | Callus calls of trumpet lily | Treated with introduction of calmodulin and $Ca^{2+}$ | 21.5 |
| Comparative Example 2 | Slice of trumpet lily leaves | Treated with introduction of distilled water | 1.4 |
| Comparative Example 3 | Callus cells of trumpet lily | Treated with introduction of distilled water | 2.3 |
| Example 4 | Callus cells of trumpet lily | Treated with introduction of calmodulin and $Ca^{2+}$ | 17.6 |
| Example 5 | Callus cells of trumpet lily | Treated with introduction of calmodulin and $Ca^{2+}$ | 18.5 |

Example 6–14

Tissue culture was applied using the same procedures as in Example 1 except for using slices of tomato leaves, callus cells of tomato, slices of eggplant leaves, callus cells of eggplant, slices of tobacco leaves, slices of trenia stalks, slices of carnation stalks, slices of cabbage hypocotyl and slices of onion scales as the material in Example 1. The results are shown in Table 2. The number of adventitious buds obtained differentiation was increased in all of the treated specimens as compared with those in Comparative Examples 4–12.

Comparative Examples 4–12

Tissue culture was applied to slices of tomato leaves, callus cells of tomato, slices of eggplant leaves, callus cells of eggplant, slices of tobacco leaves, slices of trenia stalks, slices of carnation stalks, slices of cabbage hypocotyl and slices of onion scales in the same procedures as those used in Examples 6–14 except for using distilled water instead of the calcium chloride solution containing calmodulin in the examples. The results are shown in Table 2.

TABLE 2

|  | Material | Treatment | Number of bulbs formed / slice |
|---|---|---|---|
| Example 6 | Slice of tomato leaves | Treated with introduction of calmodulin and $Ca^{2+}$ | 4.2 |
| Example 7 | Callus cells of tomato | Treated with introduction of calmodulin and $Ca^{2+}$ | 8.5 |
| Example 8 | Slice of eggplant leaves | Treated with introduction of calmodulin and $Ca^{2+}$ | 4.0 |
| Example 9 | Callus cells of eggplant | Treated with introduction of calmodulin and $Ca^{2+}$ | 6.4 |
| Example 10 | Slice of tobacco leaves | Treated with introduction of calmodulin and $Ca^{2+}$ | 7.0 |
| Example 11 | Slice of trenia stalks | Treated with introduction of calmodulin and $Ca^{2+}$ | 32.4 |
| Example 12 | Slice of carnation stalks | Treated with introduction of calmodulin and $Ca^{2+}$ | 0.7 |
| Example 13 | Slice of cabbage hypocotyl | Treated with introduction of calmodulin and $Ca^{2+}$ | 3.4 |
| Example 14 | Slice of onion scales | Treated with introduction of calmodulin and $Ca^{2+}$ | 9.8 |
| Comparative Example 4 | Slice of tomato leaves | Treated with introduction of distilled water | 2.8 |
| Comparative Example 5 | Callus cells of tomato | Treated with introduction of distilled water | 3.8 |
| Comparative Example 6 | Slice of eggplant leaves | Treated with introduction of distilled water | 2.4 |
| Comparative Example 7 | Callus cells of eggplant | Treated with introduction of distilled water | 3.2 |
| Comparative Example 8 | Slice of tobacco leaves | Treated with introduction of distilled water | 1.6 |
| Comparative Example 9 | Slice of trenia stalks | Treated with introduction of distilled water | 8.4 |
| Comparative Example 10 | Slice of carnation stalks | Treated with introduction of distilled water | 0 |
| Comparative Example 11 | Slice of cabbage hypocotyl | Treated with introduction of distilled water | 0.2 |
| Comparative Example 12 | Slice of onion scales | Treated with introduction of distilled water | 4.6 |

TABLE 3

|  | Material | Treatment | Number of bulbs formed / slice |
|---|---|---|---|
| Example 15 | Slice of basil leaves | Treated with introduction of calmodulin and $Ca^{2+}$ | 8.4 |
| Example 16 | Slice of bluebottle cotyledon | Treated with introduction of calmodulin and $Ca^{2+}$ | 7.6 |
| Example 17 | Slice of rudbeckia | Treated with introduction of calmodulin and $Ca^{2+}$ | 5.0 |
| Example 18 | Slice of tulip scales | Treated with introduction of calmodulin and $Ca^{2+}$ | 8.6 |
| Example 19 | Slice of flax scales | Treated with introduction of calmodulin and $Ca^{2+}$ | 13.8 |
| Example 20 | Slice of asparagus stalks | Treated with introduction of | 3.8 |

TABLE 3-continued

| Material | Treatment | Number of bulbs formed / slice |
|---|---|---|
| | calmodulin and $Ca^{2+}$ | |
| Comparative Example 13 | Slice of basil leaves | Treated with introduction of distilled water | 3.2 |
| Comparative Example 14 | Slice of bluebottle cotyledon | Treated with introduction of distilled water | 2.2 |
| Comparative Example 15 | Slice of rudbeckia leaves | Treated with introduction of distilled water | 2.0 |
| Comparative Example 16 | Slice of tulip leaves | Treated with introduction of distilled water | 3.8 |
| Comparative Example 17 | Slice of flax leaves | Treated with introduction of distilled water | 6.0 |
| Comparative Example 18 | Slice of asparagus stalks | Treated with introduction of distilled water | 0.6 |

Examples 15–20

Tissue culture was applied in the same procedures as in Example 1 except for using slices of basil leaves, slices of bluebottle cotyledon, slices of rudbekia leaves, slices of tulip scales, slices of flax stalks and slices of asparagus stalks, in that example and the results are shown in Table 3.

Comparative Examples 13–18

Tissue culture was applied to slices of basil leaves, slices of bluebottle cotyledon, slices of rudbekia leaves, slices of tulip scales, slices of flax stalks and slices of asparagus stalks excepting for distilled water instead of the calcium chloride solution containing calmodulin in Examples 15–20 and the results are shown in Table 3.

TABLE 4

| | Concentration in the solution | | Number of bulbs formed / slice |
|---|---|---|---|
| | $Ca^{2+}$ [mM] | Calmodulin [μg/ml] | |
| Comparative Example 19 | 0 | 0 | 2.8 |
| Example 21 | 0 | 100 | 3.5 |
| Example 22 | 0.1 | 100 | 7.5 |
| Example 23 | 0.3 | 100 | 13.0 |
| Example 24 | 1 | 100 | 14.0 |
| Example 25 | 3 | 0 | 9.5 |
| Example 26 | 3 | 10 | 10.5 |
| Example 27 | 3 | 100 | 21.5 |
| Example 28 | 10 | 100 | 11.5 |

Cultured after an aqueous solution containing Calmodulin, $Ca^{2+}$ or both at s concentration shown in the Table was introduced into cells by application of electrical pulses.

Examples 21–28 and Comparative Example 19

After cutting the scales of sterilized trumpet lily bulbs used in Example 1 to about 2 mm width, they were placed between electrodes, to which was added a solution containing calmodulin isolated and purified from the bulbs of trumpet lily at a concentration shown in Table 4 and calcium chloride at a concentration also shown in Table 4. Then, after applying electrical pulses under the same conditions as those in Example 1, the slices of trumpet lily scales were cultured in the same procedures in Example 1. The results are shown in Table 4.

Calmodulin introduced into the cells by the introduction treatment was about 33 μg/ml and the $Ca^{2+}$ concentration in the cells was increased from $10^{-7}$M to $6 \times 10^{-5}$M in Example 27.

TABLE 5

| | Material | Concentration in the solution $Ca^{2+}$ [mM] | Numbers of adventitious bulbs formed / slice |
|---|---|---|---|
| Example 29 | Slice of tobacco leaves | 1 | 2.6 |
| Example 30 | Slice of tobacco leaves | 3 | 6.2 |
| Example 31 | Slice of tobacco leaves | 10 | 4.0 |
| Example 32 | Slice of trenia stalks | 1 | 10.2 |
| Example 33 | Slice of trenia stalks | 3 | 22.6 |
| Example 34 | Slice of trenia stalks | 10 | 14.2 |
| Example 35 | Slice of onion scales | 1 | 4.8 |
| Example 36 | Slice of onion scales | 3 | 8.0 |
| Example 37 | Slice of onion scales | 10 | 5.2 |

Examples 29–37

Aqueous solutions were prepared by adding calmodulin at the concentration of 100 μg/ml to solution in Example 10, 11 and 14 containing calcium chloride at the concentrations shown in Table 5. After introducing calmodulin and calcium ion into cells using the aqueous solutions, tissue culture was applied in the same procedure as in Example 1. The results are shown in table 5.

Examples 38–40

After culturing the tissue pieces or callus for 3 to 7 days each in a medium containing $10^{-6}$M of A23187 in Examples 3, 11 and 14, electrical pulses were applied to 100 μg/ml of calmodulin solution used, and tissue culture was further applied. The results are shown in Table 6.

Examples 41–43

After conducting calmodulin introduction in the same procedures as in Example 1 using 100 μg/ml of calmodulin in Examples 3, 11 and 14, tissue culture was applied using culture medium containing $10^{-6}$M of A23187. The results are shown in Table 6.

TABLE 6

| | Material | Treatment | Number of bulbs or adventitious buds formed / slice |
|---|---|---|---|
| Example 38 | Callus cells of trumpet lily | Treated with introduction of calmodulin *1 | 18.6 (bulb) |
| Example 39 | Slice of trenia stalks | Treated with introduction of calmodulin *1 | 26.8 (adventitious bud) |
| Example 40 | Callus of onion scales | Treated with introduction of calmodulin *1 | 8.6 (adventitious bud) |
| Example 41 | Callus cells of trumpet lily | Treated with introduction of calmodulin *2 | 22.0 (bulb) |
| Example 42 | Slice of trenia stalks | Treated with introduction of calmodulin *2 | 30.6 (adventitious bud) |

TABLE 6-continued

| | Material | Treatment | Number of bulbs or adventitious buds formed / slice |
|---|---|---|---|
| Example 43 | Callus of onion scales | Treated with introduction of calmodulin *2 | 10.2 (adventitious bud) |

*1. Following tissue culture in a medium containing 1 μM calcium ionophores, cultured further after an aqueous solution containing calmodulin at a concentration of 100 μg/ml was introduced into cells.
*2. Cultured in a medium containing 1 μM calcium ionophores after an aqueous solution containing calmodulin at a concentration of 100 μg/ml was introduced into cells.

TABLE 7

| | Material | Treatment | Number of adventitious embryo/external slice (0.1 g) |
|---|---|---|---|
| Example 44 | Slice of carrot hypocotyl | Treated with introduction of calmodulin and $Ca^{2+}$ | 0.4 |
| Example 45 | Callus cells of soybean | Treated with introduction of calmodulin and $Ca^{2+}$ | 1.0 |
| Example 46 | Callus cells of cucumber | Treated with introduction of calmodulin and $Ca^{2+}$ | 2.4 |
| Example 47 | Callus cells of rice | Treated with introduction of calmodulin and $Ca^{2+}$ | 2.2 |
| Example 48 | Callus cells of snapdragon | Treated with introduction of calmodulin and $Ca^{2+}$ | 3.6 |
| Example 49 | Callus cells of asparagus | Treated with introduction of calmodulin and $Ca^{2+}$ | 4.2 |
| Comparative Example 20 | Slice of carrot hypocotyl | Treated with introduction of distilled water | 0 |
| Comparative Example 21 | Callus cells of soybean | Treated with introduction of distilled water | 0 |
| Comparative Example 22 | Callus cells of cucumber | Treated with introduction of distilled water | 0 |
| Comparative Example 23 | Callus cells of soybean | Treated with introduction of distilled water | 0.8 |
| Comparative Example 24 | Callus cells of snapdragon | Treated with introduction of distilled water | 0.6 |
| Comparative Example 25 | Callus cells of asparagus | Treated with introduction of distilled water | 2.4 |

Examples 44-49

Tissue culture was applied in the same procedures as in Example 1 except for using slices of carrot hypocotyl, callus cells of soybean, callus cells of cucumber, callus cells of rice, callus cells of snapdragon, callus cells of asparagus as the material in that example and the results are shown in Table 7. The number of adventitious embryos obtained by differentiation was increased in all of treated specimens as compared with those in Comparative Examples 20-25.

Comparative Examples 20-25

Slices of carrot hypocotyl, callus cells of soybean, callus cells of cucumber, callus cells of rice, callus cells of snapdragon, callus cells of asparagus were cultured in the same procedures as in Example 1 excepting for using distilled water instead of using the calcium chloride solution containing calmodulin in Examples 44-49.

Examples 50-52

Slices of asparagus callus stalks were applied with tissue culture in the same manner as in Example 1 using solutions containing calmodulin in Example 20 at concentrations shown in Table 8 and calcium chloride at concentrations also shown in Table 8 and the results are shown in Table 8. The number of adventitious buds obtained by the differentiation was increased in all of the treated specimens as compared with that in Comparative Example 26, and the diameter of the stalks was also increased as that in Comparative Example 26.

Comparative Example 26

Slices of asparagus stalks were cultured in the same procedures as in Examples 50-52 except for using distilled water instead of the calcium chloride solution containing calmodulin in these examples.

TABLE 8

| | Concentration in solution | | Number of adventitious buds formed / slice | Adventitious buds diameter (mm) |
|---|---|---|---|---|
| | $Ca^{2+}$ [mM] | calmodulin [μg/ml] | | |
| Comparative Example 26 | 0 | 0 | 0.5 | 1.1 |
| Example 50 | 0 | 100 | 2.4 | 2.3 |
| Example 51 | 1 | 100 | 3.2 | 2.6 |
| Example 52 | 3 | 100 | 4.4 | 4.2 |

TABLE 9

| | Material | Treatment | Number of adventitious buds foromed/callus slice (0.1 g) |
|---|---|---|---|
| Example 53 | Callus slice of miniature rose | Treated with introduction of calmodulin | 5.2 |
| Comparative Example 27 | Callus slice of miniature rose | Treated with introduction of distilled water | 2.4 |

Example 53

Tissue culture was applied in the same procedures as in Example 1 except for using callus cells induced from the slices of stalks and slices of leaves of miniature rose (variety: Marie Antoinette) in that example. The results are shown in Table 9. The number of the treated adventitious buds was increased as compared with that in Comparative Example 27.

Comparative Example 27

Callus cells of miniature rose were cultured in the same procedures as in Example 53 except for using distilled water instead of the calcium chloride solution containing calmodulin in Example 53.

Comparative Example 28

Slices of trumpet lily bulb scales were cultured in the same procedure as in Example 1 except that the procedure of introducing calmodulin and calcium ions by application of electrical pulses using an aqueous, calmodulin-containing solution of calcium chloride was not carried out. As a result, the number of bulbs formed per slice was 2.3 and was almost the same as the result(2.8pieces) of Comparative Example 19 where slices were cultured after application of electrical pulses using distilled water.

Comparative Example 29-31

Slice of trumpet lily bulb scales were cultured in the same procedure and Murashige and Skoog solid culture medium as in Example 1 except that no electrical pulses were used and instead the medium contained A23187 calcium ionophores at the concentrations shown in Experiment Group(1)in Table 10. The results are shown in Table 10.

Comparative Example 32, 34, 36, 42, 44, and 48

Tissue culture was applied in the same procedure as in Comparative Example 28 except for replacement of the slices of trumpet lily bulb scales cultured in Comparative Example 28 by the plant samples set forth in the Table 10. The results are shown in Table 10.

Comparative Example 33, 35, 39, 41, 43, 47, and 49

Tissue culture was applied in the same procedure as in Comparative Example 30 except for replacement of the slices of trumpet lily bulb scales cultured in Comparative Example 30 by the plant samples set forth in Table 10. The results are shown in Table 10.

TABLE 10

| | Material | Treatment | The number / slice*[1] |
|---|---|---|---|
| (1) Example 1 | Slice of trumpet lily scales | Treated with introduction of calmodulin and $Ca^{2+}$ | 4.7 (bulb) |
| Comparative Example 1 | Slice of trumpet lily scales | Treated with introduction of distilled water | 2.1 (bulb) |
| Comparative Example 28 | Slice of trumpet lily scales | No treatment*[2] | 2.3 (bulb) |
| Comparative Example 29 | Slice of trumpet lily scales | No treatment and culture in a medium containing A23187 (0.1 $\mu$M) | 4.7 (bulb) |
| Comparative Example 30 | Slice of trumpet lily scales | No treatment and culture in a medium containing A23187 (1 $\mu$M) | 6.1 (bulb) |
| Comparative Example 31 | Slice of trumpet lily scales | No treatment and culture in a medium containing A23187 (10 $\mu$M) | 3.2 (bulb) |
| (2) Example 13 | Slice of cabbage hypocoptyl | Treated with introduction of calmodulin and $Ca^{2+}$ | 3.4 (adventitious bud) |
| Comparative Example 11 | Slice of cabbage hypocoptyl | Treated with introduction of distilled water | 0.2 (adventitious bud) |
| Comparative Example 32 | Slice of cabbage hypocoptyl | No treatment | 1.2 (adventitious bud) |
| Comparative Example 33 | Slice of cabbage hypocoptyl | No treatment and culture in a medium containing A23187 (1 $\mu$M) | 3.4 (adventitous bud) |
| (3) Example 15 | Slice of basil leaves | Treated with introduction of calmodulin and $Ca^{2+}$ | 8.4 (adventitious bud) |
| Comparative Example 13 | Slice of basil leaves | Treated with introduction of distilled water | 8.4 (adventitious bud) |
| Comparative Example 34 | Slice of basil leaves | No treatment | 3.2 (adventitious bud) |
| Comparative Example 35 | Slice of basil leaves | No treatment and culture in a medium containing A23187 (1 $\mu$M) | 7.4 (adventitious bud) |
| (4) Example 17 | Slice of rudbekia leaves | Treated with introduction of calmodulin and $Ca^{2+}$ | 5.0 (adventitious bud) |
| Comparative Example 15 | Slice of rudbekia leaves | Treated with introduction of distilled water | 2.0 (adventitious bud) |
| Comparative Example 36 | Slice of rudbekia leaves | No treatment | 2.5 (adventitious bud) |
| Comparative Example 37 | Slice of rudbekia leaves | No treatment and culture in a medium containing A23187 (1 $\mu$M) | 5.6 (adventitious bud) |
| (5) Example 17 | Callus cells of tomato | Treated with introduction of calmodulin and $Ca^{2+}$ | 8.5 (adventitious bud) |
| Comparative Example 5 | Callus cells of tomato | Treated with introduction of distilled water | 3.8 (adventitious bud) |
| Comparative Example 38 | Callus cells of tomato | No treatment | 3.4 (adventitious bud) |
| Comparative Example 39 | Callus cells of tomato | No treatment and culture in a medium containing A23187 (1 $\mu$M) | 7.8 (adventitious bud) |
| (6) Example 9 | Callus cells of eggplant | Treated with introduction of calmodulin and $Ca^{2+}$ | 6.4 (adventitious bud) |
| Comparative Example 7 | Callus cells of eggplant | Treated with introduction of distilled water | 3.2 (adventitious bud) |
| Comparative Example 40 | Callus cells of eggplant | No treatment | 3.0 (adventitious bud) |
| Comparative Example 41 | Callus cells of eggplant | No treatment and culture in a medium containing A23187 (1 $\mu$M) | 5.6 (adventitious bud) |
| (7) Example 44 | Slice of carrot hypocoptyl | Treated with introduction of calmodulin and $Ca^{2+}$ | 0.4 (adventitious embryo) |
| Comparative Example 20 | Slice of carrot hypocoptyl | Treated with introduction of distilled water | 0.0 (adventitious embryo) |
| Comparative Example 42 | Slice of carrot hypocoptyl | No treatment | 2.4 (adventitious embryo) |
| Comparative Example 43 | Slice of carrot hypocoptyl | No treatment and culture in a medium containing A23187 (1 $\mu$M) | 4.2 (adventitious embryo) |
| (8) Example 14 | Slice of onion scales | Treated with introduction of calmodulin and $Ca^{2+}$ | 9.8 (bulb) |
| Comparative Example 12 | Slice of onion scales | Treated with introduction of distilled water | 4.6 (bulb) |
| Comparative Example 44 | Slice of onion scales | No treatment | 6.8 (bulb) |
| Comparative Example 45 | Slice of onion scales | No treatment and culture in a medium containing A23187 (1 $\mu$M) | 12.8 (bulb) |
| Example 43 | Slice of onion scales | cultured in medium containing A23187 (1 $\mu$M) after introduction of | 10.2 (bulb) |

TABLE 10-continued

| | Material | Treatment | The number / slice*[1] |
|---|---|---|---|
| Example 40 | Slice of onion scales | calomdulin introduction of calmodulin following culture in a medium containing A23187 (1 μM) | 8.6 (bulb) |
| (9) Example 18 | Slice of tulip scales | Treated with introduction of calmodulin and Ca$^{2+}$ | 8.6 (bulb) |
| Comparative Example 16 | Slice of tulip scales | Treated with introduction of distilled water | 3.8 (bulb) |
| Comparative Example 46 | Slice of tulip scales | No treatment | 4.2 (bulb) |
| Comparative Example 47 | Slice of tulip scales | No treatment and culture in a medium containing A23187 (1 μM) | 8.8 (bulb) |
| (10) Example 47 | Callus cells of rice | Treated with introduction of calmodulin and Ca$^{2+}$ | 2.2 (adventitious embryo) |
| Comparative Example 23 | Callus cells of rice | Treated with introduction of distilled water | 0.8 (adventitious embryo) |
| Comparative Example 48 | Callus cells of rice | No treatment | 0.8 (adventitious embryo) |
| Comparative Example 49 | Callus cells of rice | No treatment and culture in a medium containing A23187 (1 μM) | 2.4 (adventitious embryo) |

*[1]The number / slice indicates number of bulbs, adventitious buds or adventitious embryo / slice.
*[2]No treatment indicates no application of electrical pulses.
*Calmodulin; 100 μg/ml, Ca$^{2+}$; 3 mM

What is claimed is:

1. A method of inducing the formation of adventitious buds, adventitious embryos, or bulbets of a plant comprising:
   (a) subjecting plant tissue pieces or callus in an aqueous solution to electrical pulses at from 30 V/cm to 2.5 KV/cm for 30 μsec to 1 msec to produce a calmodulin concentration of from 10 μg/ml to 100 μg/ml inside of the cells, wherein the calmodulin concentration of said aqueous solution is from 3 μg/ml to 1 mg/ml, and thereafter
   (b) culturing the tissue pieces or the callus in an artificial culture medium.

2. The method of claim 1, wherein the artificial culture medium is Murashige and Skoog medium containing sucrose, naphthalenecarboxylic acid and benzyl adenine.

3. A method of inducing the formation of adventitious buds, adventitious embryos, or bulbets of a plant comprising:
   (a) subjecting plant tissue pieces or callus in an aqueous solution to electrical pulses at from 30 V/cm to 2.5 KV/cm for 30 μsec to 1 msec to produce a calcium ion concentration of from $10^{-8}$M to $10^{-5}$M inside of the cells, wherein the calcium ion concentration of said aqueous solution is from 100 μM to 30 mM, and thereafter
   (b) culturing the tissue pieces or the callus in an artificial culture medium.

4. The method of claim 3 wherein the artificial culture medium is Murashige and Skoog medium containing sucrose, naphthalenecarboxylic acid and benzyl adenine.

5. A method of inducing the formation of adventitious buds, adventitious embryos, or bulbets of a plant comprising:
   (a) subjecting plant tissue pieces or callus in an aqueous solution to electrical pulses at from 30 V/cm to 2.5 KV/cm for 30 μsec to 1 msec to produce a calmodulin concentration of from 10 μg/ml to 100 μg/ml and a calcium ion concentration of from $10^{-8}$M to $10^{-5}$M inside of the cells, wherein the calmodulin concentration of said aqueous solution is from 3 μg/ml to 1 mg/ml and the calcium ion concentration of said aqueous solution is from 100 μM to 30 mM, and thereafter
   (b) culturing the tissue pieces or the callus in an artificial culture medium.

6. The method of claim 5, wherein the artificial culture medium is Murashige and Skoog medium containing sucrose, naphthalenecarboxylic acid and benzyl adenine.

* * * * *